United States Patent
Agbodoe

(10) Patent No.: US 6,991,633 B2
(45) Date of Patent: Jan. 31, 2006

(54) RONGEUR WITH DETACHABLE CROSSBAR

(75) Inventor: Victor Bandford Agbodoe, Stoughton, MA (US)

(73) Assignee: Codman & Shurtleff, Inc., Raynham, MA (US)

( * ) Notice: Subject to any disclaimer, the term of this patent is extended or adjusted under 35 U.S.C. 154(b) by 269 days.

(21) Appl. No.: 10/403,230

(22) Filed: Mar. 31, 2003

(65) Prior Publication Data

US 2003/0187450 A1 Oct. 2, 2003

Related U.S. Application Data

(63) Continuation-in-part of application No. 09/974,404, filed on Oct. 10, 2001, now Pat. No. 6,685,710.

(51) Int. Cl.
*A61B 17/00* (2006.01)

(52) U.S. Cl. .............................. 606/83; 606/170; 606/79
(58) Field of Classification Search ................... 606/79, 606/83, 170, 184
See application file for complete search history.

(56) References Cited

U.S. PATENT DOCUMENTS

| | | | | |
|---|---|---|---|---|
| 2,113,246 A | * | 4/1938 | Wappler | 606/205 |
| 2,790,437 A | * | 4/1957 | Moore | 600/564 |
| 3,777,538 A | * | 12/1973 | Weatherly et al. | 72/409.01 |
| 3,814,102 A | * | 6/1974 | Thai | 606/207 |
| 4,043,343 A | * | 8/1977 | Williams | 606/207 |
| 4,084,594 A | * | 4/1978 | Mosior | 606/170 |
| 4,569,131 A | * | 2/1986 | Falk et al. | 30/251 |
| 4,722,338 A | * | 2/1988 | Wright et al. | 606/83 |
| 4,896,678 A | * | 1/1990 | Ogawa | 600/564 |
| 4,990,148 A | * | 2/1991 | Worrick et al. | 606/83 |
| 5,009,661 A | * | 4/1991 | Michelson | 606/170 |

(Continued)

FOREIGN PATENT DOCUMENTS

| | | | |
|---|---|---|---|
| DE | 19748369 A1 | * | 5/1999 |
| DE | 29922271 U1 | * | 4/2000 |
| EP | 1 212 983 | | 6/2002 |
| WO | 02/059815 A | | 9/2002 |

*Primary Examiner*—Kevin Shaver
*Assistant Examiner*—Candice C. Stokes

(57) ABSTRACT

A rongeur has a detachable crossbar to enhance cleaning and sterilization. A pin in a slot on one of the rongeur's handles is moveable out of the slot to permit extended retraction of the crossbar to a position in which it may disengage from the shank of the rongeur.

14 Claims, 8 Drawing Sheets

U.S. PATENT DOCUMENTS

| | | | | |
|---|---|---|---|---|
| 5,026,375 A | * | 6/1991 | Linovitz et al. | 606/79 |
| 5,061,269 A | * | 10/1991 | Muller | 606/83 |
| 5,147,357 A | * | 9/1992 | Rose et al. | 606/49 |
| 5,147,378 A | * | 9/1992 | Markham | 606/206 |
| 5,156,608 A | * | 10/1992 | Troidl et al. | 606/142 |
| 5,273,519 A | * | 12/1993 | Koros et al. | 606/83 |
| 5,282,800 A | * | 2/1994 | Foshee et al. | 606/52 |
| 5,312,407 A | * | 5/1994 | Carter | 606/79 |
| 5,336,238 A | * | 8/1994 | Holmes et al. | 606/208 |
| 5,342,391 A | * | 8/1994 | Foshee et al. | 606/205 |
| 5,385,570 A | * | 1/1995 | Chin et al. | 606/170 |
| 5,451,227 A | | 9/1995 | Michaelson | 606/83 |
| 5,484,441 A | * | 1/1996 | Koros et al. | 606/79 |
| 5,496,347 A | * | 3/1996 | Hashiguchi et al. | 606/205 |
| 5,507,772 A | * | 4/1996 | Shutt et al. | 606/205 |
| 5,507,774 A | * | 4/1996 | Holmes et al. | 606/208 |
| 5,527,339 A | * | 6/1996 | Koscher et al. | 606/205 |
| 5,569,258 A | * | 10/1996 | Gambale | 606/83 |
| 5,569,298 A | | 10/1996 | Schnell | |
| 5,582,618 A | * | 12/1996 | Chin et al. | 606/170 |
| 5,584,844 A | * | 12/1996 | Weisshaupt | 606/170 |
| 5,613,977 A | * | 3/1997 | Weber et al. | 606/170 |
| 5,618,308 A | * | 4/1997 | Holmes et al. | 606/205 |
| 5,630,832 A | * | 5/1997 | Giordano et al. | 606/208 |
| 5,649,958 A | * | 7/1997 | Grimm et al. | 606/208 |
| 5,653,713 A | * | 8/1997 | Michelson | 606/83 |
| 5,718,714 A | * | 2/1998 | Livneh | 606/205 |
| 5,766,177 A | * | 6/1998 | Lucas-Dean et al. | 606/83 |
| 5,851,214 A | * | 12/1998 | Larsen et al. | 606/170 |
| 5,879,365 A | * | 3/1999 | Whitfield et al. | 606/180 |
| 5,961,531 A | * | 10/1999 | Weber et al. | 606/167 |
| 6,063,103 A | * | 5/2000 | Hashiguchi | 606/205 |
| 6,077,290 A | * | 6/2000 | Marini | 606/205 |
| 6,126,674 A | * | 10/2000 | Janzen | 606/206 |
| 6,200,320 B1 | * | 3/2001 | Michelson | 606/83 |

* cited by examiner

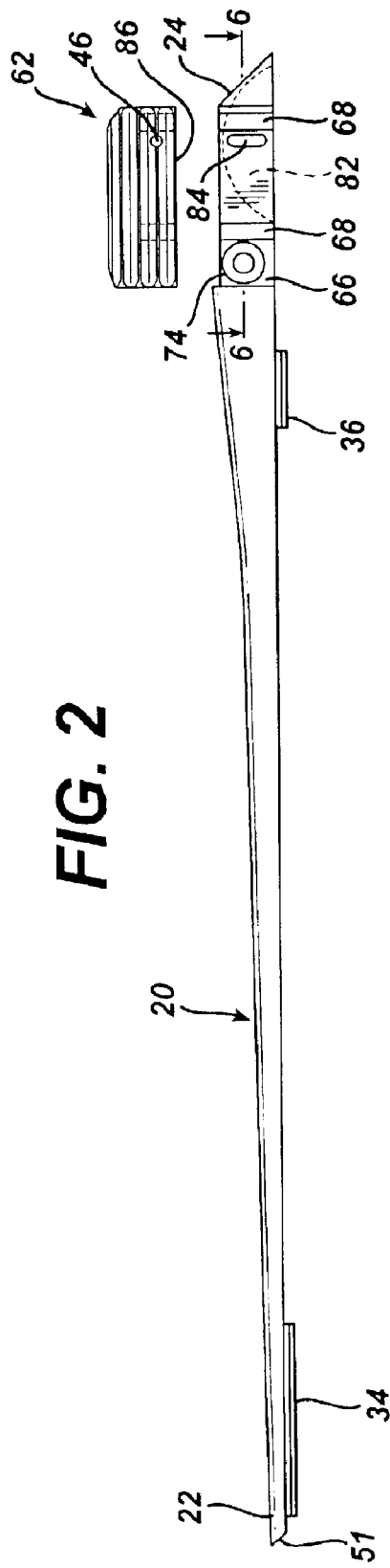
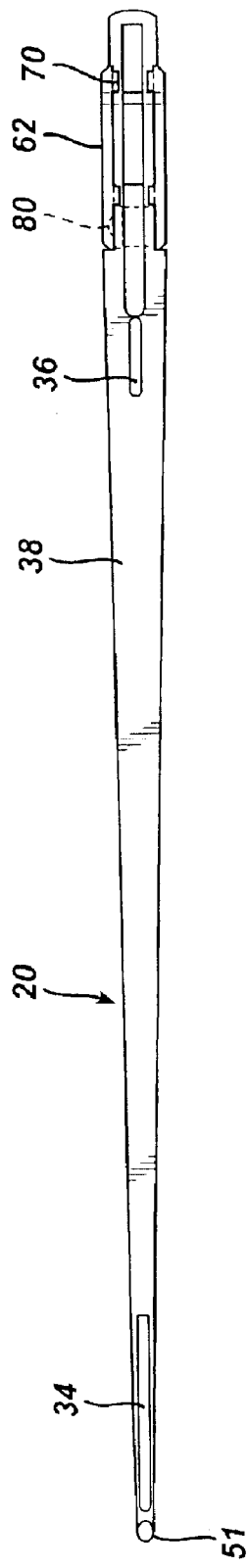

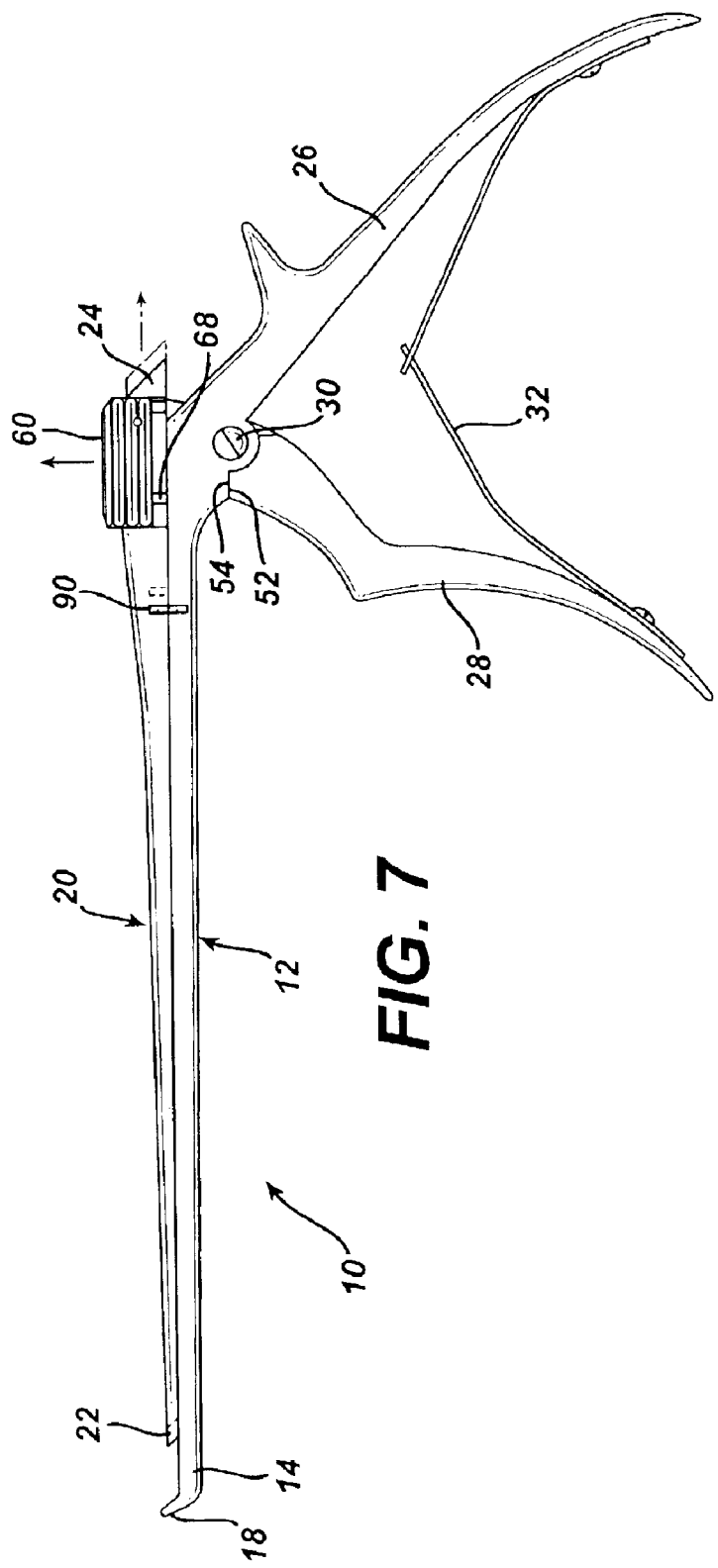
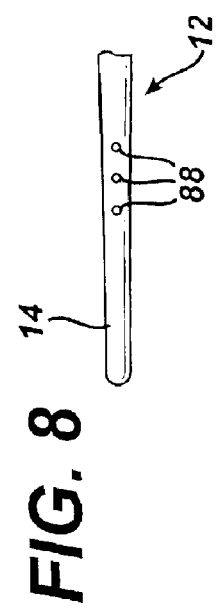
FIG. 7
FIG. 8

RONGEUR WITH DETACHABLE CROSSBAR

CONTINUING INFORMATION

This application is a continuation-in-part of application Ser. No. 09/974,404, filed Oct. 10, 2001, now U.S. Pat. No. 6,685,710, the disclosure of which is hereby fully incorporated by reference.

FIELD OF THE INVENTION

The present invention relates to a rongeur, and more particularly to a rongeur having a detachable crossbar.

BACKGROUND

The rongeur is a medical instrument used for a variety of purposes. It is particularly useful for removing small amounts of bone, cartilage or other body material from inside small spaces of the knee or between vertebrae. A rongeur usually includes a long fixed shank with an anvil or footplate at its distal end and a handle at its proximal end. A cross bar slideably engages the shank and reciprocates thereon by means of a pivotable second handle. Cutting edges on the distal end of the crossbar bite against the footplate to cut away a small portion of tissue with each reciprocation of the crossbar.

For precise operation of the instrument tight tolerances between the mating parts is preferred. While enhancing precise operation, these tolerances can make effective cleaning of the instrument difficult. Blood and other bodily matter with becomes trapped between the shank and crossbar can be difficult to remove. Failure to remove such matter can lead to incomplete sterilization. Accordingly, it is desirable to allow access to these parts during cleaning and sterilization.

The Janzen U.S. Pat. No. 6,126,674, incorporated herein by reference, attempts to solve this problem by providing a removable crossbar. A slot in the top of the pivotable handle receives a pin on the crossbar. A rotating disc on the fixed handle abuts a surface on the pivotable handle to limit spread between the handles. Rotation of the disc into an alternate orientation allow a slightly broader spread between the handles allowing the crossbar to move back distally off of the pin and to then be removed. In such a design it can be difficult to balance the force necessary to rotate the disc. If the force required is too great it can be difficult to operate and discourage disassembly prior to sterilization. If the force required is too low it can allow the device to disassemble accidentally during normal use.

SUMMARY OF THE INVENTION

A rongeur according to the present invention overcomes these and other limitations of the prior art. It comprises an elongated shank having a distal end and a proximal end and an elongated crossbar having a distal end and a proximal end adapted to reciprocate axially with respect to the shank. The crossbar has a retracted position wherein the crossbar is partially retracted proximally with respect to the shank and a retracted-release position wherein the crossbar is further retracted proximally with respect to the shank than in the retracted position. Mating surfaces on the shank and crossbar align to block disengagement of the crossbar from the shank in the retracted positions and come out of alignment to allow disengagement of the crossbar from the shank in the retracted-release position. A first handle is fixedly configured to the shank proximal end and a second handle pivotably attaches to the shank proximal end about a pivot axis. A slot in an upper portion of the second handle receives a pin affixed to the crossbar at its proximal end whereby pivoting of the second handle about the pivot axis induces axial movement of the pin to reciprocate the crossbar. Engagement between the pin and the slot prevents the crossbar from retracting to the retracting-release position. The pin is selectively moveable upwardly sufficiently out of the slot to allow further proximal movement of the crossbar with respect to the shank to the retracted-release position whereby to allow the crossbar to be disengaged and removed from the shank for more effective cleaning and sterilization thereof. The pin is positioned on a holding member on the crossbar, the holding member having a first position in which the pin is sufficiently deeply within the slot to prevent retraction of the crossbar to the retracted-released position and a second position in which the pin is sufficiently out of the slot so as to allow retraction of the crossbar to the retracted-release position. A stop screw has a head and a threaded shank. The threaded shank is threadably engaged with the crossbar between a first position, which prevents movement of the holding member from its first position to its second position, and a second position, which permits movement of the holding member from its first position to its second position.

Preferably the mating surfaces comprise an undercut slot on one of the shank and crossbar and a flange on the other of the shank and crossbar received within the slot, and more preferably the slot and flange are T-shaped. Preferably, a proximal portion of the slot is not undercut.

Preferably, a detent engagement is provided between the holding member and the crossbar when the holding member is in its first position, which engagement can comprise a spring ball. In one aspect of the invention, the holding member has a U-shaped cross section and is received over the crossbar. The pin can penetrate an aperture on the crossbar to fix the holding member to the crossbar. Preferably, the crossbar has a vertical groove and the holding member has a rib on an inner surface thereof which slides within the vertical groove.

Preferably, one or more of drainage apertures penetrate through the shank adjacent the footplate. The drainage apertures can penetrate through the shank at the slot.

BRIEF DESCRIPTION OF THE DRAWINGS

FIG. 2 is a front elevation view of a crossbar from the rongeur of FIG. 1;

FIG. 3 is a bottom plan view of the crossbar of FIG. 2;

FIG. 7 is a front elevation view of the rongeur of FIG. 1 showing the locking mechanism in the unlocked orientation;

FIG. 8 is a bottom plan view of a distal portion of the rongeur of FIG. 1;

DETAILED DESCRIPTION

Figure 1:
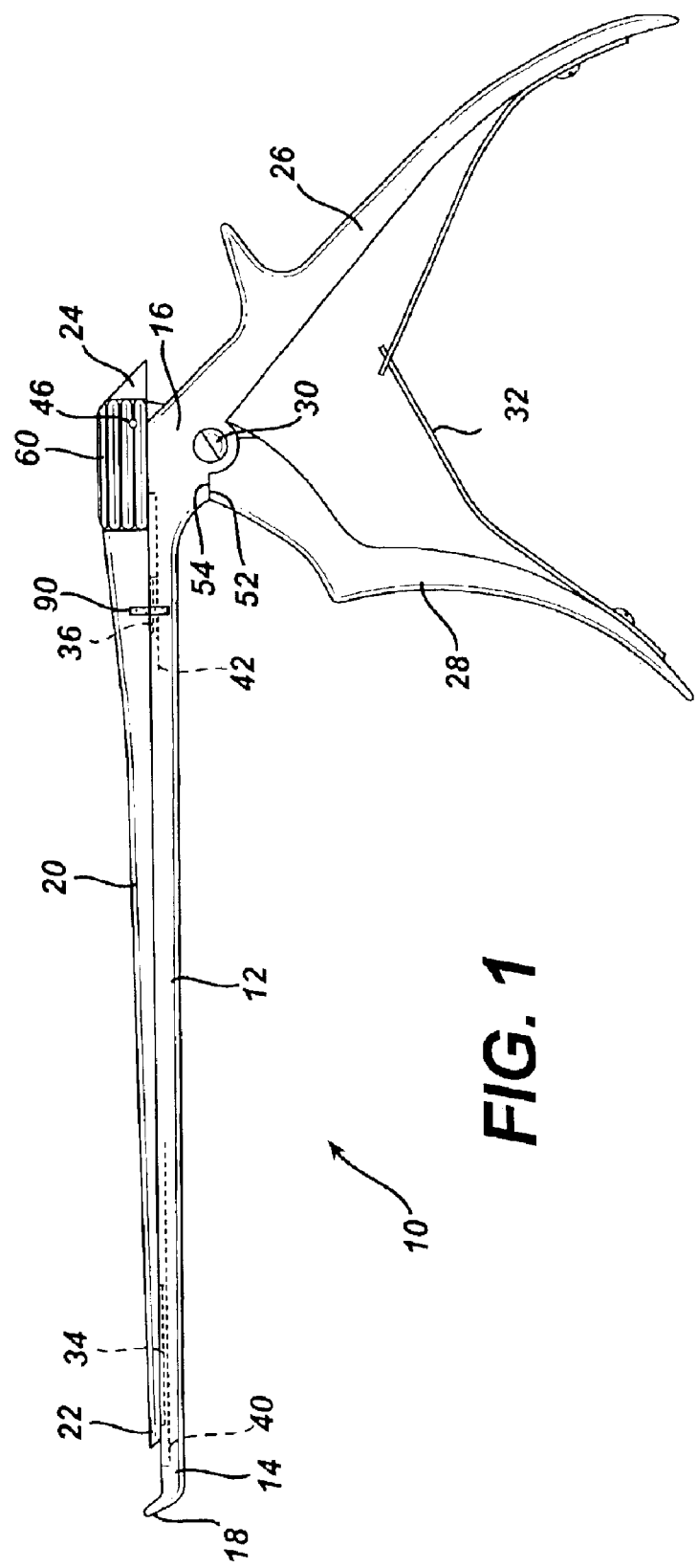
FIG. 1 is a front elevation view of a rongeur according to the present invention.

FIG. 1 illustrates a rongeur 10 according to the present invention. It comprises an elongated shank 12 having a distal end 14 and proximal end 16. A footplate 18 extends upwardly from the shank 12 at its distal end 14. A crossbar 20 slideably engages the shank 12 and also comprises a distal end 22 and proximal end 24. A first handle 26 extends downwardly from the shank proximal end 16 in fixed relation to the shank 12. A second handle 28 pivotably attaches to the shank 12 near its proximal end 16 and pivots about an axis 30. A spring 32 between the first and second handles 26 and 28 biases them apart.

As further seen in FIGS. 2 and 3, distal and proximal T-shaped splines 34 and 36, respectively, on a lower surface 38 of the crossbar 20 fit within respective distal and proximal T-shaped slots, 40 and 42, respectively, on an upper surface 44 of the shank 12 to allow slideable axial movement between the crossbar 20 and shank 12 without allowing the crossbar 20 to lift off of the shank 12. It will be appreciated by one of skill in the art that the locations of the splines and slots can be reversed and that other engaging shapes can be substituted therefor.

Figure 4:
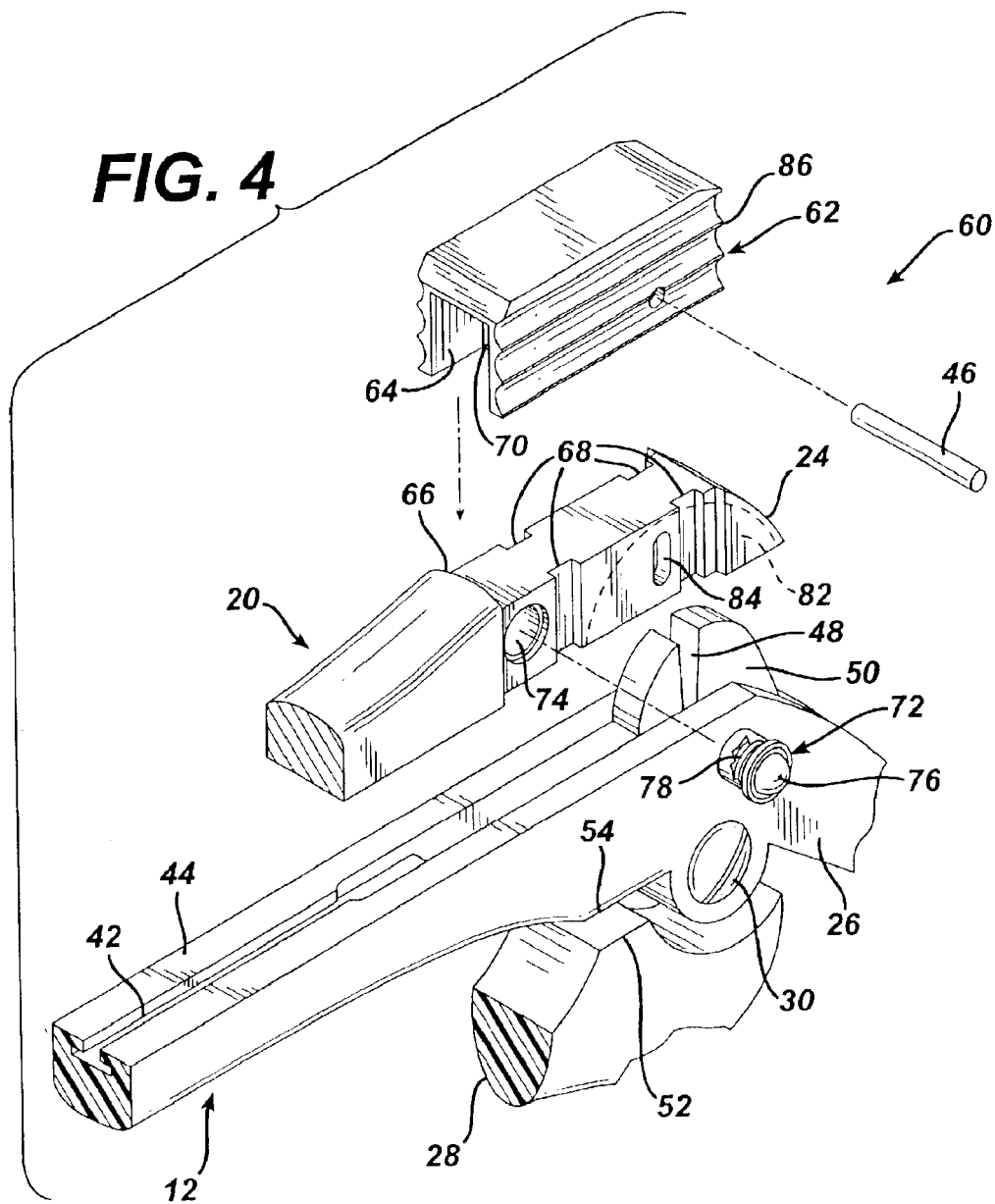
FIG. 4 is an exploded perspective view of a locking mechanism of the rongeur of FIG. 1.
Figure 5:
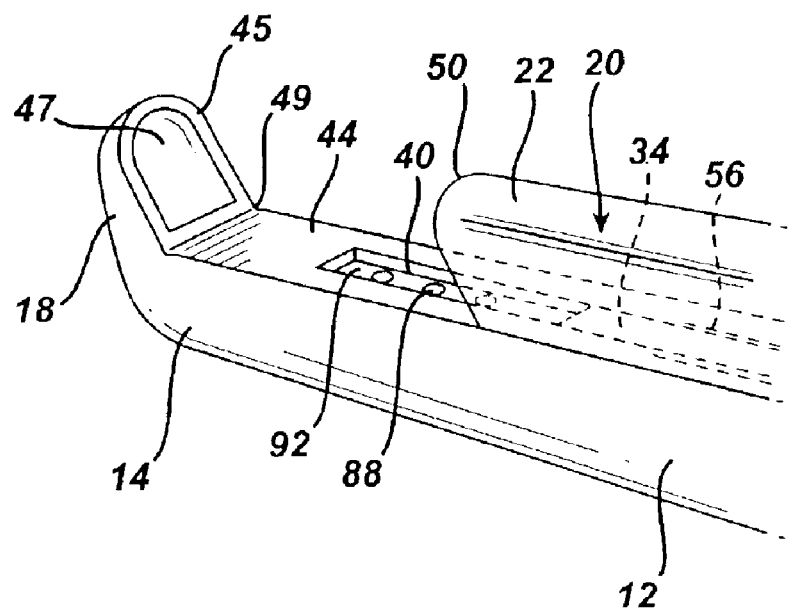
FIG. 5 is a perspective detail view of a footplate on the rongeur of FIG. 1

Turning further to FIG. 4, a pin 46 on the crossbar 20 rides within a slot 48 on an upper portion 50 of the second handle 28 so that when the second handle 28 is squeezed toward the first handle 26 by an operator the slot 48 moves distally and the action of the pin 46 therein drives the crossbar 20 distally. Turning further to FIG. 5, the footplate 18 comprises an anvil cutting surface 45 about a tissue receiving recess 47 and a stress relieving groove 49 between the footplate 18 and shank 12 as more fully described in U.S. Pat. No. 4,990,148 to Worrick, III et al., fully incorporated herein by reference. Cutting edges 51 on the distal end 22 of the crossbar 20 engage the anvil surface 45 whereby tissue, as for instance bone, trapped therebetween is cut.

It is advantageous to disassemble the rongeur 10, by removing the crossbar 20, prior to cleaning and sterilizing. Focusing primarily upon FIG. 4, removal of the crossbar 20 is effected by moving the pin 46 upwardly out of the slot 48. Contact between a handle abutment surface 52 on the second handle 28 and a shank abutment surface 54 on the shank 12 limits rotation of the second handle 28 and thus effectively limits rearward or proximal movement of the crossbar 20. Proximal portions 56 and 58 respectively of the distal slot 40 and proximal slot 42 are open, not T-shaped, so as to allow disengagement of the splines 34 and 36 from the slots 40 and 42 and thereby allow the crossbar 20 to be lifted off of the shank 12. To disengage the splines 34 and 36 they must be in register with the proximal portions 56 and 58. However, abutment of the handle and shank abutment surfaces 52 and 54 limits proximal movement of the crossbar 20 sufficiently to disallow registry of the splines 34 and 36 with the proximal portions 56 and 58. Moving the pin 46 upwardly out of the slot 48 allows further proximal movement of the crossbar 20 so as to allow registry of the splines 34 and 36 with the proximal portions 56 and 58 and thus removal of the crossbar 20.

Figure 6:
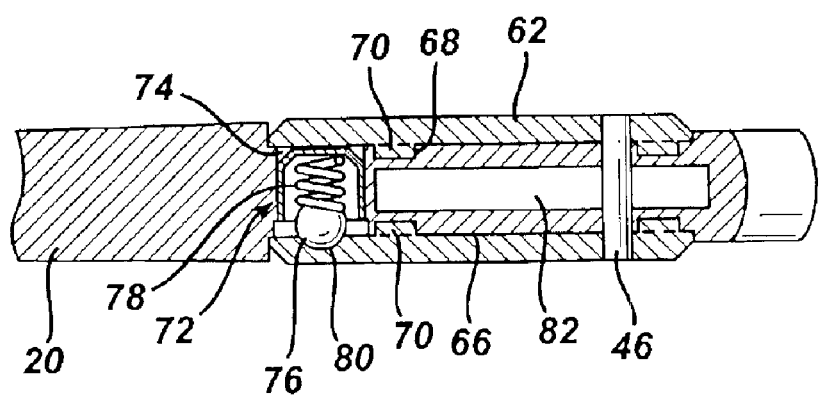
FIG. 6 is a cross sectional view taken along lines 6—6 of FIG. 2.
Figure 9:
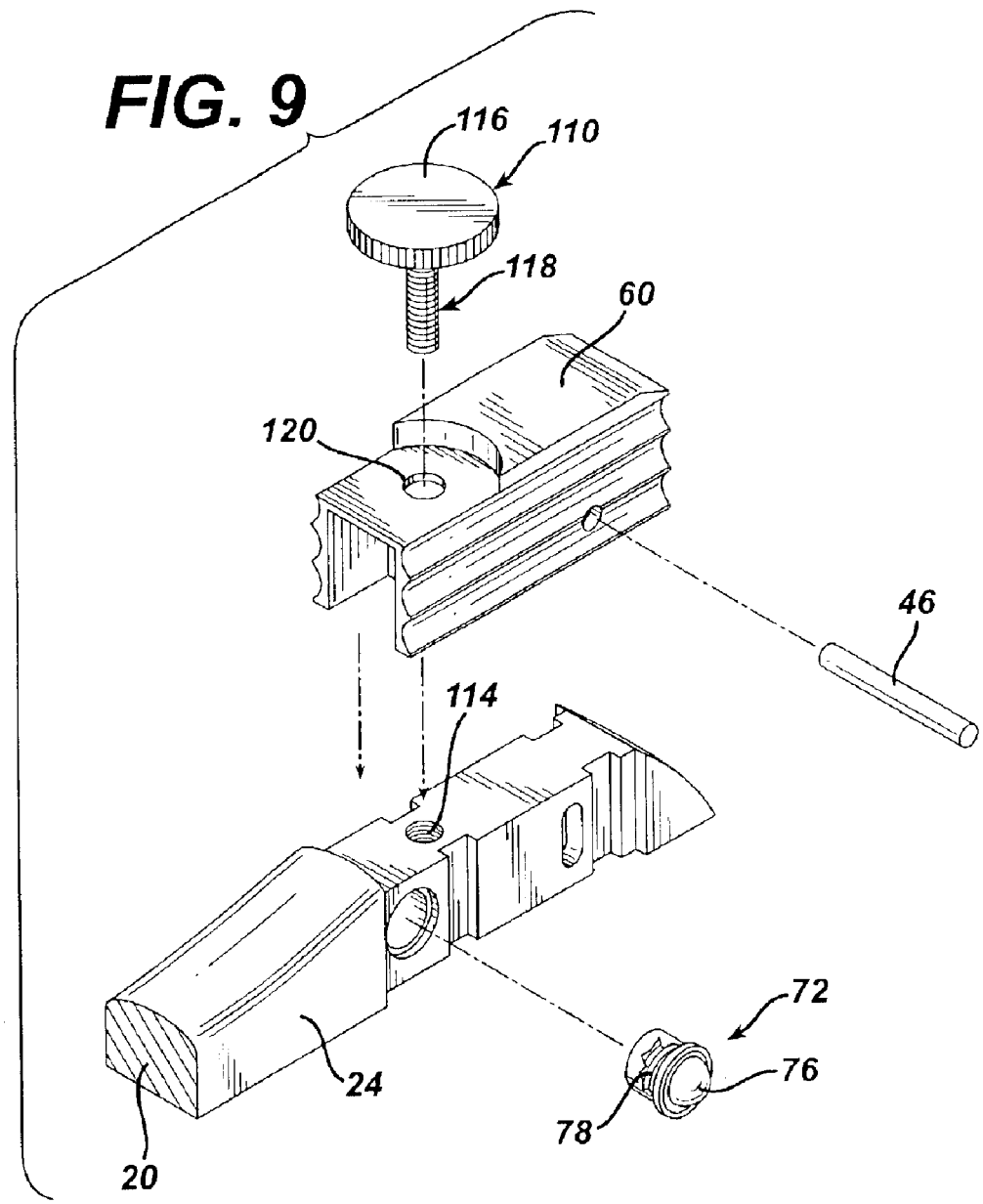
FIG. 9 is a partial exploded view showing the holding member and safety screw in accordance with another embodiment of the present invention.
Figure 10:
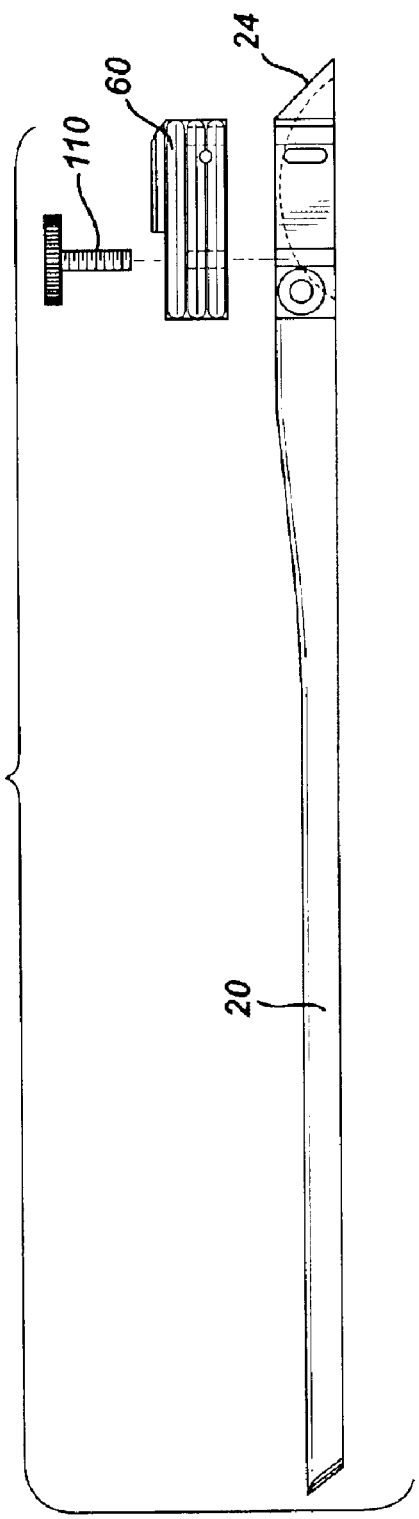
FIG. 10 is an exploded front elevation view of the crossbar of FIG. 9.
Figure 11:
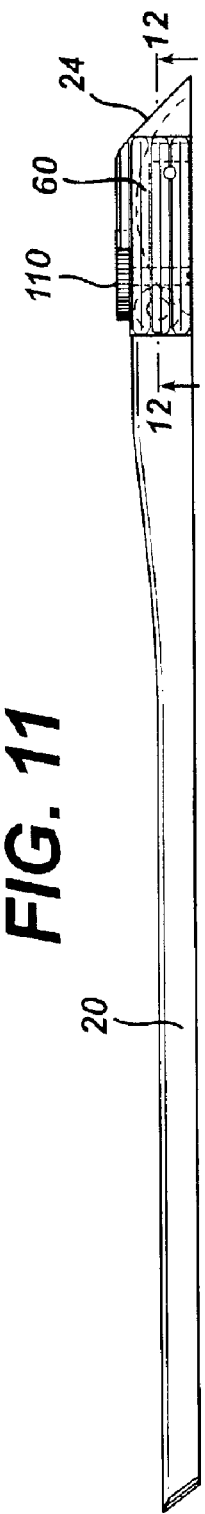
FIG. 11 is front elevation view of the crossbar of FIG. 9.
Figure 12:
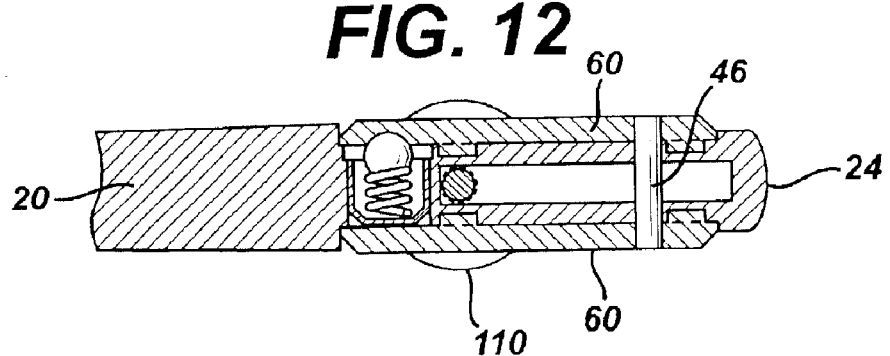
FIG. 12 is a cross sectional view taken along lines 12—12 of FIG. 11.
Figure 13:
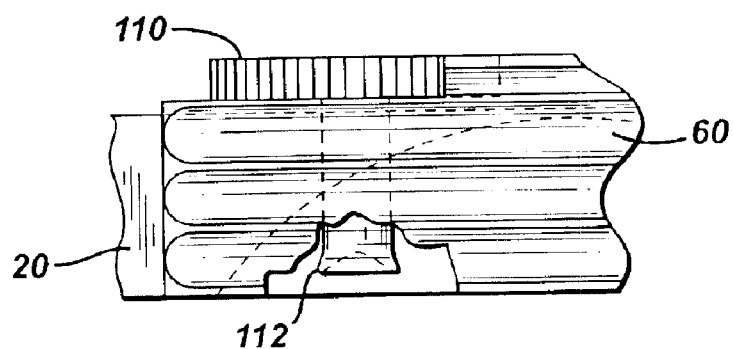
FIG. 13 is a partial front elevation view of the holding member in its first position.
Figure 14:
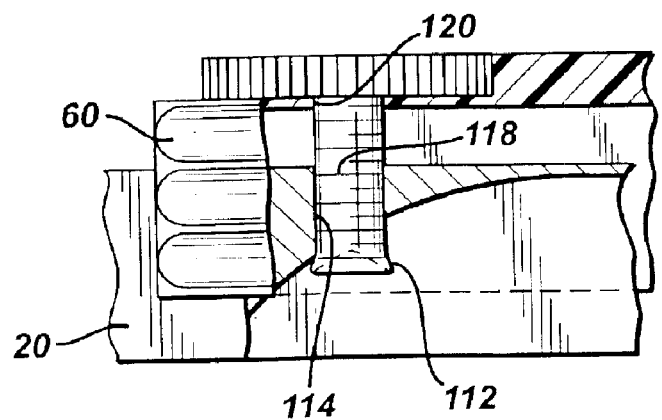
FIG. 14 is a partial front elevation view, with parts broken away, of the holding member in its second position.

A locking mechanism 60 maintains the pin 46 within the slot 48 and allows its selective movement thereout. The locking mechanism 60 comprises a channel member 62 having a lower channel 64 which fits over a recessed portion 66 of the crossbar 20 near its proximal end 24. Vertically oriented guiding grooves 68 on the recessed portion 66 receive mating tongues 70 to guide vertical movement of the channel member 62 on the crossbar 20. The pin 46 passes laterally through the channel member 62 and is affixed thereto. A spring ball plunger 72 on the received within an aperture 74 on the crossbar comprises a caged ball 76 and spring 78 (see also FIG. 6). The ball 76 engages a dimple 80 on an inner surface of the channel 64 to hold the channel member in a lowered position. Sufficient upward force on the channel member 62 disengages the ball 76 from the dimple 80 to allow the channel member 62 to move upwardly.

As primarily seen in FIGS. 2 and 4, an arcuate undercut chamber 82 on the crossbar 20 receives the second handle upper portion 50. The pin 46 passes through elongated vertical slots 84 in the crossbar 20 and sits in the slot 48 in the second handle upper portion 50. With the pin 46 trapped in the elongated slots 84 the channel member 62 is thus held to the crossbar 20, even when lifted to an upper position as shown in FIG. 7. Preferably, gripping enhancements such as ribbing 86 shown in FIG. 4 is provided on the channel member 62.

Turning primarily to FIG. 8, drainage holes 88 penetrate the shank 12 near its distal end 14. These drainage holes allow drainage of blood and bodily fluids during use and allow drainage during cleaning. They may be countersunk on a surface 92 facing the crossbar 20 as shown in FIG. 5 to encourage drainage into the holes 88. Further, the surface 92 can be sloped toward the holes 88 to enhance drainage therethrough.

In use, the first and second handles 26 and 28 are squeezed together to move the second handle upper portion 50 distally thereby engaging the pin 46 and driving the crossbar 20 distally. The cutting edges 51 on the crossbar distal end 22 move toward the anvil 45 and tissue (not shown) trapped therebetween is cut away. Typically, many successive cuts are made in one procedure. Blood and bodily fluid within the distal slot 40 are allowed to pass out through the drainage holes 88. After the cutting procedure is over, the channel member 62 is lifted up and the crossbar moved proximally to a retracted release position, as shown in phantom in FIG. 7. In this position the T-shaped splines 34 and 36 align with the open proximal portions 56 and 58 of the slots 40 and 42. The crossbar 20 is then lifted free of the shank 12. Cleaning and sterilization of the rongeur 10 is effected in this disassembled state.

To reassemble the rongeur 10, the channel member 62 is placed in its upward position and the splines 34 and 36 are moved into the proximal portions 56 and 58 of the slots 40 and 42. The crossbar is moved distally to engage the T-shaped splines 34 and 36 within the T-shaped slots 40 and 42 and to place the pin 46 in location over the slot 48 on the second handle upper portion 50. A pair of alignment marks 90 on the shank 12 and crossbar 20 can be provided to assist in locating this position. Then, the channel member is pressed down to engage the pin 46 into the slot 48 and the spring ball plunger 72 into the dimple 80.

Referring now to FIGS. 9–14, another embodiment of the present invention is illustrated. This embodiment incorporates a stop screw 110 to prevent inadvertent upward movement of the holding member 60. Because most of the elements in this embodiment are identical to those discussed above, for the sake of brevity in the disclosure, only those elements that vary from the above embodiment will be discussed in detail. A stop screw 110 has a head 116 and a threaded shank 118. The threaded shank 118 threadably engages a threaded bore 114 within the crossbar 20. Threaded shank is axially movable within bore 114 between a first position (see FIGS. 11–13), which prevents movement of the holding member 60 from its first lowered position to its second upward position, and a second position, which permits movement of the holding member 60 from its first lowered position to its second upward position. Holding member 60 has an aperture 120. Threaded shank 118 passes through aperture 120 in holding member 60. A distal end of the threaded shank 118 remote from head 116 has a radially outwardly flared end 112 to prevent screw 110 from being removed from crossbar 20.

The invention now being fully described, it will be apparent to one of ordinary skill in the art that many modifications and changes can be made thereto without departing from the spirit or scope of the invention as defined in the following claims.

What is claimed is:

1. A rongeur comprising:

an elongated shank having a distal end and a proximal end;

an elongated crossbar having a distal end and a proximal end adapted to reciprocate axially with respect to the shank;

the crossbar having a retracted position wherein the crossbar is partially retracted proximally with respect to the shank and a retracted-release position wherein the crossbar is further retracted proximally with respect to the shank than in the retracted position;

mating surfaces on the shank and crossbar which are aligned to block disengagement of the crossbar from the shank when it is in the retracted positions and which are out of alignment to allow disengagement of the crossbar from the shank when it is in the retracted-release position;

a first handle fixedly configured to the shank proximal end and a second handle pivotably attached to the shank proximal end about a pivot axis;

a slot in an upper portion of the second handle and a pin affixed to the crossbar at its proximal end receivable within the slot whereby pivoting of the second handle about the pivot axis induces axial movement of the pin whereby to reciprocate the crossbar, the engagement between the pin and the slot preventing the crossbar from retracting to the retracting-release position; and the pin being selectively moveable upwardly sufficiently out of the slot to allow further proximal movement of the crossbar with respect to the shank to the retracted-release position whereby to allow the crossbar to be disengaged and removed from the shank for more effective cleaning and sterilization thereof, the pin is positioned on a holding member on the crossbar, the holding member having a first position in which the pin is disposed sufficiently deeply within the slot to prevent retraction of the crossbar to the retracted-released position and a second position in which the pin is disposed sufficiently out of the slot so as to allow retraction of the crossbar to the retracted-release position, further comprising a stop screw having a head and a threaded shank, the threaded shank being threadably engaged with the crossbar between a first position, which prevents movement of the holding member from its first position to its second position, and a second position, which permits movement of the holding member from its first position to its second position.

2. A rongeur according to claim 1 wherein the mating surfaces comprise an undercut slot on one of the shank and crossbar and a flange on the other of the shank and crossbar received within the slot.

3. A rongeur according to claim 2 wherein the slot is T-shaped and the flange is T-shaped.

4. A rongeur according to claim 2 wherein a proximal portion of the slot is not undercut.

5. A rongeur according to claim 1 and further comprising a detent engagement between the holding member and the crossbar when the holding member is in its first position.

6. A rongeur according to claim 5 wherein the detent engagement comprises a spring ball.

7. A rongeur according to claim 1 wherein the holding member has a U-shaped cross section and is received over the crossbar.

8. A rongeur according to claim 7 wherein the crossbar has a vertical groove and the holding member has a rib on an inner surface thereof which slides within the vertical groove.

9. A rongeur according to claim 1 wherein the pin penetrates an aperture on the crossbar to fix the holding member to the crossbar.

10. A rongeur according to claim 1 further comprising a footplate at the distal end of the elongated shaft, the shank having one or more of drainage apertures through the shank adjacent the footplate.

11. A rongeur according to claim 10 wherein the shank comprises a slot on an upper surface thereof and the crossbar comprises a spline on a lower surface thereof, the spline being disposed within the slot, and wherein the one or more drainage apertures penetrate the shank into the slot.

12. A rongeur according to claim 1 and further comprising an alignment mark on one of the crossbar and shank to indicate proper alignment of the pin with respect to the slot prior to engaging the pin therein.

13. A rongeur according to claim 1 wherein the holding member has an aperture, the threaded shank passes through the aperture in the holding member.

14. A rongeur according to claim 1 wherein a distal end of the threaded shank remote from the head has a radially outwardly flared end.

* * * * *